(12) United States Patent
Bahmer

(10) Patent No.: US 9,042,994 B2
(45) Date of Patent: May 26, 2015

(54) TEMPORAL CODING FOR HEARING IMPLANTS

(71) Applicant: MED-EL Elektromedizinische Geraete GmbH, Innsbruck (AT)

(72) Inventor: Andreas Bahmer, Aschaffenburg (DE)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 0 days.

(21) Appl. No.: 14/061,245

(22) Filed: Oct. 23, 2013

(65) Prior Publication Data

US 2014/0121725 A1    May 1, 2014

Related U.S. Application Data

(60) Provisional application No. 61/720,600, filed on Oct. 31, 2012.

(51) Int. Cl.
*A61N 1/00* (2006.01)
*A61N 1/36* (2006.01)
*A61N 1/05* (2006.01)

(52) U.S. Cl.
CPC ........... *A61N 1/36032* (2013.01); *A61N 1/0541* (2013.01)

(58) Field of Classification Search
CPC .......................... A61N 1/0541; A61N 1/36032
USPC ............................................................. 607/57
See application file for complete search history.

(56) References Cited

U.S. PATENT DOCUMENTS

| 6,594,525 | B1 | 7/2003 | Zierhofer | 607/57 |
|---|---|---|---|---|
| 7,004,906 | B1 | 2/2006 | Guracar et al. | 600/447 |
| 7,149,583 | B1* | 12/2006 | Litvak | 607/57 |
| 7,917,224 | B2 | 3/2011 | Zierhofer | 607/57 |
| 2006/0235490 | A1* | 10/2006 | Killian et al. | 607/60 |
| 2007/0270949 | A1 | 11/2007 | Paolini et al. | 623/10 |
| 2008/0125832 | A1 | 5/2008 | Horsager et al. | 607/54 |
| 2011/0077712 | A1 | 3/2011 | Killian | 607/57 |

FOREIGN PATENT DOCUMENTS

WO    WO 2012/106207    8/2012    ............ A61N 1/36

OTHER PUBLICATIONS

International Searching Authority, International Search Report—International Application No. PCT/US13/66375, dated Mar. 27, 2014, together with the Written Opinion of the International Searching Authority, 21 pages.
Wilson et al., "Better Speech Recognition With Cochlear Implants", Nature, vol. 352, pp. 236-238, 1991.
Victor et al., "A new statistic for steady-state evoked potentials", Electroencephalography and Clinical Neurophysiology, vol. 78, pp. 378-388, 1991.

(Continued)

*Primary Examiner* — George Manuel
(74) *Attorney, Agent, or Firm* — Sunstein Kann Murphy & Timbers LLP

(57) ABSTRACT

A system and method is provided for activating electrodes in a multi-channel electrode array having electrodes that are spatially divided. At least one pulse for stimulating a single electrode of the electrode array is determined. Each of the pulses is converted into a plurality of pulses for stimulating a plurality of electrodes in the electrode array.

50 Claims, 4 Drawing Sheets

(56) References Cited

OTHER PUBLICATIONS

John et al., "Human auditory steady-state responses to amplitude-modulated tones: phase and latency measurements", Hearing Research, vol. 141, pp. 57-79, 2000.

John et al., "MASTER: a Windows program for recording multiple auditory steady-state responses", Computer Methods and Programs in Biomedicine, vol. 61, pp. 125-150, 2000.

Laback et al., "Binaural jitter improves interaural time-difference sensitivity of cochlear implantees at high pulse rates", Proceedings of the National Academy of Sciences, vol. 105, No. 2, pp. 814-817, Jan. 15, 2008.

Bahmer et al., Recording and online analysis of auditory steady state responses (ASSR) in Matlab, Journal of Neuroscience Methods, vol. 187, pp. 105-113, Mar. 15, 2010.

Bahmer et al., "Parameters for a model of an oscillating neuronal network in the cochlear nucleus defined by genetic algorithms", Biological Cybernetics, vol. 102, pp. 81-93, 2010.

Bahmer, "Temporal information transfer with cochlear implants: Improvements and Measurements", Frankfurt am Main, 121 pages, 2012.

\* cited by examiner

TEMPORAL CODING FOR HEARING IMPLANTS

CROSS-REFERENCE TO RELATED APPLICATIONS

This application claims priority from U.S. provisional patent application Ser. No. 61/720,600 filed Oct. 31, 2012, entitled "Temporal Coding for Hearing Implants," which is hereby incorporated herein by reference in its entirety.

TECHNICAL FIELD

The present invention relates to temporal coding for hearing implants, and more particularly to evaluation and methodology of temporal coding for a cochlear implant.

BACKGROUND ART

A human ear normally transmits sounds such as speech sounds as shown in FIG. 1 through the outer ear 101 to the tympanic membrane (eardrum) 102, which moves the bones of the middle ear 103 (malleus, incus, and stapes) that vibrate the oval window membrane of the cochlea 104. The cochlea 104 is a long narrow duct wound spirally about its axis for approximately two and three quarters turns. It includes three chambers along its length: an upper chamber known as the scala vestibuli, a middle chamber known as the scala media, and a lower chamber known as the scala tympani. The cochlea 104 forms an upright spiraling cone with a center called the modiolus where the axons of the auditory nerve 113 reside. These axons project in one direction to the cochlear nucleus in the brainstem and they project in the other direction to the spiral ganglion cells and neural processes peripheral to the cells (hereinafter called peripheral processes) in the cochlea. In response to received sounds transmitted by the middle ear 103, sensory hair cells in the cochlea 104 function as transducers to convert mechanical motion and energy into electrical discharges in the auditory nerve 113. These discharges are conveyed to the cochlear nucleus and patterns of induced neural activity in the nucleus are then conveyed to other structures in the brain for further auditory processing and perception.

Hearing is impaired when there are problems in the ability to transduce external sounds into meaningful action potentials along the neural substrate of the cochlea 104. In some cases, hearing impairment can be addressed by an auditory prosthesis system such as a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing, and produces a stimulation pattern (based on the extracted audio information) that is sent through an electrode lead 109 to an implanted electrode array 112 which penetrates into the cochlea 104 through a surgical opening called a cochleostomy. Typically, this electrode array 112 includes multiple electrode contacts 110 on its surface that deliver the stimulation signals to adjacent neural tissue of the cochlea 104 which the brain of the patient interprets as sound. The individual electrode contacts 110 may be activated using various stimulation strategies that include, for example, sequential or simultaneous stimulation in one or more contact groups.

The representation of temporal information in an auditory system by use of cochlea implants is imperfect compared to a normal functioning hearing organ. In a healthy ear, temporal information is recorded by the hair cells and their corresponding nerve fibers before the information is translated to the brain. Up to a certain frequency, the hair cells can follow the externally generated acoustic information in phase with the corresponding oscillation of the basilar membrane. However, the nerve fibers have a certain refractory period which allows only a limited temporal coding. In case of a healthy physiological system, there are sufficient nerve fibers present having different refractory states after stimulation. Consequently, acting as an ensemble, these nerve fibers together are typically able to represent temporal information up to 5 kHz (see, for example, Wever and Bray's "volley theory," 1937).

In case of a cochlear implant, the temporal information is provided via the electrodes by, for example, biphasic electrical pulses which directly elicit action potentials in the nerve fibers. As a consequence, all nerve fibers around an electrical contact of the cochlear implant electrode are elicited synchronously and the volley principal is not applicable any more. Transfer of temporal information may thus be strongly impaired.

The coupling to the neuronal system is therefore imperfect with regard to a cochlear implant. Further, conditions like the actual impedance of the cochlear implant's electrode contacts may be different from patient to patient. As a consequence, standardized pulse sequences may be sub-optimal for patients. To help address this problem, psycho-acoustic tests have been performed in which the patient provides subjective feedback whether he is able to discriminate pitch of presented sounds at various pulse rates. (See Bahmer and Baumann 2012, Cochlear Implants International, accepted). However, such subjection feedback can vary depending on the circumstances, and may be hard to achieve with certain patients, for example, small children.

SUMMARY OF THE EMBODIMENTS

In accordance with an embodiment of the invention, a method is provided for activating electrodes in a multi-channel electrode array having electrodes that are spatially divided. The method includes determining at least one pulse for stimulating a single electrode of the electrode array. Each of the pulses is converted into a plurality of pulses for stimulating a plurality of electrodes in the electrode array.

In accordance with related embodiments of the invention, converting may include adding temporal separation between at least two pulses associated with different electrodes. The pulses for stimulating a plurality of electrodes may be at a supra-threshold pulse or a sub-threshold pulse. The energy of the plurality of pulses may be substantially equal to the energy of the pulse for stimulating the first electrode. The temporal and/or spatial center of mass for the plurality of pulses may be substantially equivalent to that of the determined pulse. The plurality of pulses may vary in amplitude, pulse length, and/or temporal separation. The variation may be based on a Gaussian distribution, a Poisson distribution, and/or a uniform Distribution. The at least one pulse for stimulating a single electrode of the electrode array may be a plurality of pulses that form a sequential pulse sequence, such as a Continuous Interleaved Sampling (CIS) speech signal processing strategy.

In accordance with still further related embodiments of the invention, the method may further include stimulating the plurality of electrodes based, at least in part, on the converted pulses. The electrode array may be part of an auditory prosthesis that is implanted in a user, the method further including performing at least one neurophysiologic measurement upon stimulating the electrodes, and evaluating the neurophysiologic measurements so as to determine the quality of temporal coding for enhanced pitch discrimination. The at least one neurophysiologic measurement may include electrically evoked auditory steady state responses (EASSR), electrically evoked brainstem response audiometry (EBERA), near field measurements, and/or electrically evoked compound action potentials (ECAP). Evaluating the neurophysiologic measurements may include statistical testing and/or use of a genetic algorithm. The pulse rate may be adjusted based on the evaluation. The multi-channel electrode may be associated with an implant. The multi-channel electrode array may be associated with a cochlear implant, a brain stem implant, or deep brain stimulation.

In accordance with another embodiment of the invention, an auditory prosthesis system includes a stimulator adapted to be implantable, the stimulator including a plurality of electrodes forming a multi-channel electrode array. A processor is configured to determine at least one pulse for stimulating a single electrode of the electrode array. The processor is further configured to convert each of the pulses into a plurality of pulses for stimulating a plurality of electrodes in the electrode array.

In accordance with related embodiments of the invention, the processor may be configured to add temporal separation between at least two converted pulses associated with different electrodes. The pulses for stimulating the plurality of electrodes may be a supra-threshold pulse or a sub-threshold pulse. The energy of the plurality of pulses may be substantially equal to the energy of the determined pulse for stimulating the first electrode. The temporal and/or spatial center of mass for the plurality of pulses may be substantially equivalent to that of the determined pulse. The plurality of pulses may vary in amplitude, pulse length, and/or temporal separation. The variation may be based on a Gaussian distribution, a Poisson distribution, and/or a uniform Distribution. The at least one pulse for stimulating a single electrode of the electrode array may be a plurality of pulses that form a sequential pulse sequence. The sequential pulse sequence may be based on a Continuous Interleaved Sampling (CIS) speech signal processing strategy.25. The stimulator may be configured to stimulate the plurality of electrodes based, at least in part, on the converted pulses.

In accordance with still further embodiments of the invention, the test module may be configured to perform at least one neurophysiologic measurement on a user of the prosthesis to the electrode stimulation. The test module may be further configured to evaluate the neurophysiologic measurements so as to determine the quality of temporal coding for enhanced pitch discrimination. Evaluating the neurophysiologic measurements may include statistical testing and/or use of a genetic algorithm. The neurophysiologic measurement may include electrically evoked auditory steady state responses (EASSR), electrically evoked brainstem response audiometry (EBERA), near field measurements, and/or electrically evoked compound action potentials (ECAP).

In accordance with another embodiment of the invention, a method of evaluating the quality of temporal coding for enhanced pitch discrimination associated with a auditory prosthesis is provided. The auditory prosthesis includes a plurality of electrodes in a multi-channel electrode array. The method includes stimulating the electrodes at a pulse rate. At least one neurophysiologic measurement is performed on a user of the prosthesis to the electrode stimulation. The neurophysiologic measurements are evaluated so as to determine the quality of temporal coding for enhanced pitch discrimination. The pulse pattern and/or rate is adjusted based on the evaluation.

In accordance with related embodiments of the invention, the neurophysiologic measurement may include electrically evoked auditory steady state responses (EASSR), electrically evoked brainstem response audiometry (EBERA), near field measurements, and/or electrically evoked compound action potentials (ECAP). Evaluating the neurophysiologic measurements may include statistical testing and/or using a genetic algorithm. Performing the at least one neurophysiologic measurement may be done without subjective feedback from the user.

In accordance with another embodiment of the invention, an auditory prosthesis system includes a plurality of electrodes in a multi-channel electrode array. A stimulator is configured to stimulate the electrodes at a pulse rate. The system further includes means for performing at least one neurophysiologic measurement on a user of the prosthesis to the electrode stimulation, means for evaluating the neurophysiologic measurements so as to determine the quality of temporal coding for enhanced pitch discrimination; and means for adjusting the pulse pattern and/or rate based on the evaluation.

In accordance with related embodiments of the invention, the neurophysiologic measurement may include electrically evoked auditory steady state responses (EASSR), electrically evoked brainstem response audiometry (EBERA), near field measurements, and/or electrically evoked compound action potentials (ECAP). The means for evaluating the neurophysiologic measurements may include statistical testing and/or use of a genetic algorithm. The means for performing the at least one neurophysiologic measurement may be done without subjective feedback from the user.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiment of the invention, enhanced pulse stimulation sequences are identified that accurately represent temporal information to hearing implant users. The modified pulse sequences may be patient specific, such that they differ from user to user. In further embodiments of the invention, neurophysiologic measurements for a hearing implant are used as the basis for evaluating the quality of temporal coding for enhanced pitch discrimination. The neurophysiologic measurements may be taken without, or used in combination with, subjective feedback from the user of the implant. Details are discussed below.

Figure 2:
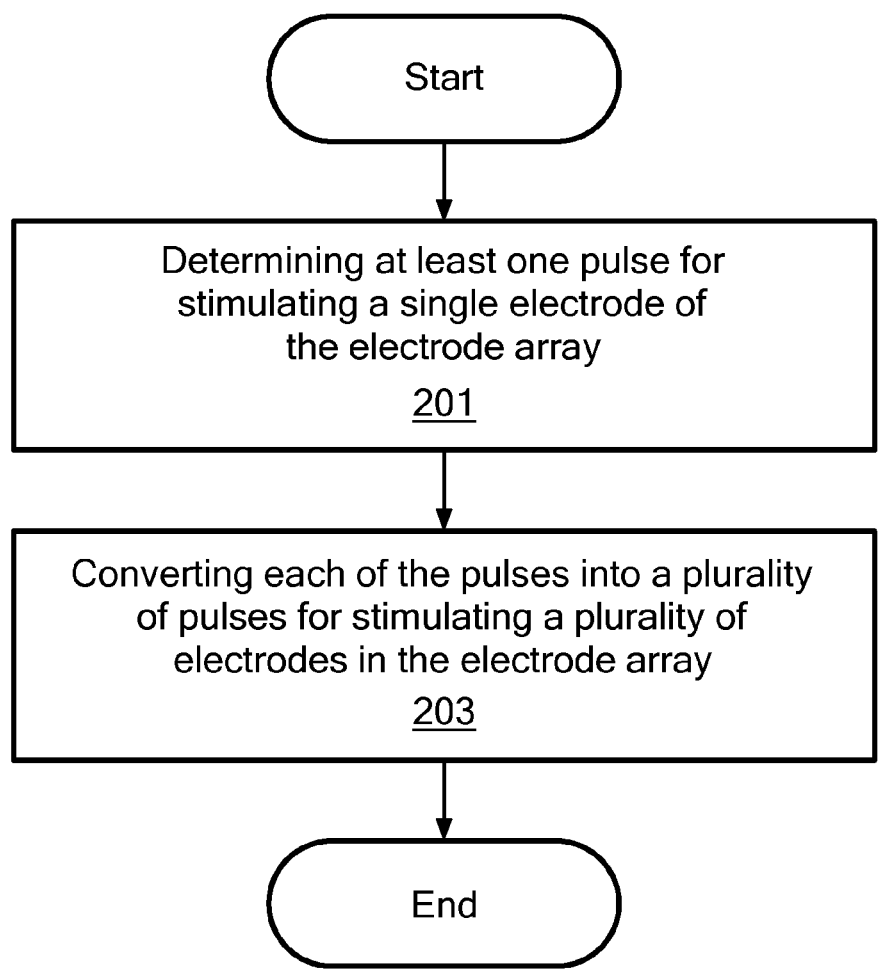
FIG. 2 shows a flow chart illustrating a method of activating electrodes in a multi-channel electrode array, in accordance with an embodiment of the invention.

FIG. 2 shows a flow chart illustrating a method of activating electrodes in a multi-channel electrode array, in accordance with an embodiment of the invention. The multi-channel electrode array may be associated with an implant. The implant may be any implant known in the art that includes pulsed stimulation. For example, the multi-channel electrode array may be associated with a hearing implant, such as a cochlear implant, in which the electrodes of the electrode are positioned such that they are spatially divided within the cochlea. The cochlear implant may be partially implanted, and include, without limitation, an external speech processor, microphone and/or coil, with an implanted stimulator and/or electrode array. In other embodiments, the cochlear implant may be a totally implanted cochlear implant. In further embodiments, the multi-channel electrode may be associated with deep brain stimulation (DBS) or a brainstem implant, such as an auditory brainstem implant.

At least one pulse is determined for stimulating a single electrode of the electrode array, step 201. In various embodiments, the implant employs a stimulation strategy that provides pulsatile stimuli in a multi-channel electrode array. The at least one pulse may be, without limitation, a plurality of pulses that form a sequential pulse sequence for a given electrode. One specific example of a stimulation strategy is the "Continuous Interleaved Sampling (CIS)"-strategy, as described by Wilson et al., Better Speech Recognition With Cochlear Implants, Nature, vol. 352:236-238 (1991), which is incorporated herein by reference in its entirety. For CIS, symmetrical biphasic current pulses are used, which are strictly non-overlapping in time across the plurality of electrodes. The rate per channel typically is higher than 800 pulses/sec. It is to be understood that the invention is not limited to CIS strategies, and is applicable with other stimulation strategies known in the art, such as, but not limited to, simultaneous activation/overlapping of electrode currents. For example, and without limitation, one such simultaneous stimulation is described in U.S. Pat. No. 6,594,525 (Zierhofer), which is incorporated herein by reference in its entirety.

Each of the pulses is converted into a plurality of pulses for stimulating a plurality of electrodes in the electrode array, step 203. For example, instead of presenting a pulse sequence comprising n individual pulses on a single electrode channel (main channel), each of the n individual pulses associated with the pulse sequence may be transformed into a composite of pulses. Each of those composites of pulses may comprise pulses distributed over several electrode channels (main and neighboring channels; spatial separation) and, in addition, temporal jitter between each pulses of the composite (temporal separation) may be introduced. The pulses in the composite of pulses may be supra- and/or subthreshold. Acting as an ensemble, the composite of pulses advantageously allows enhanced representation/interpretation of the temporal information. Involving several channels instead of just one, the use of composite pulses leads to a spread of temporal information to a larger and more distributed number of nerve fibers, thus reducing the problem of eliciting the corresponding nerve fibers synchronously.

Figure 3:
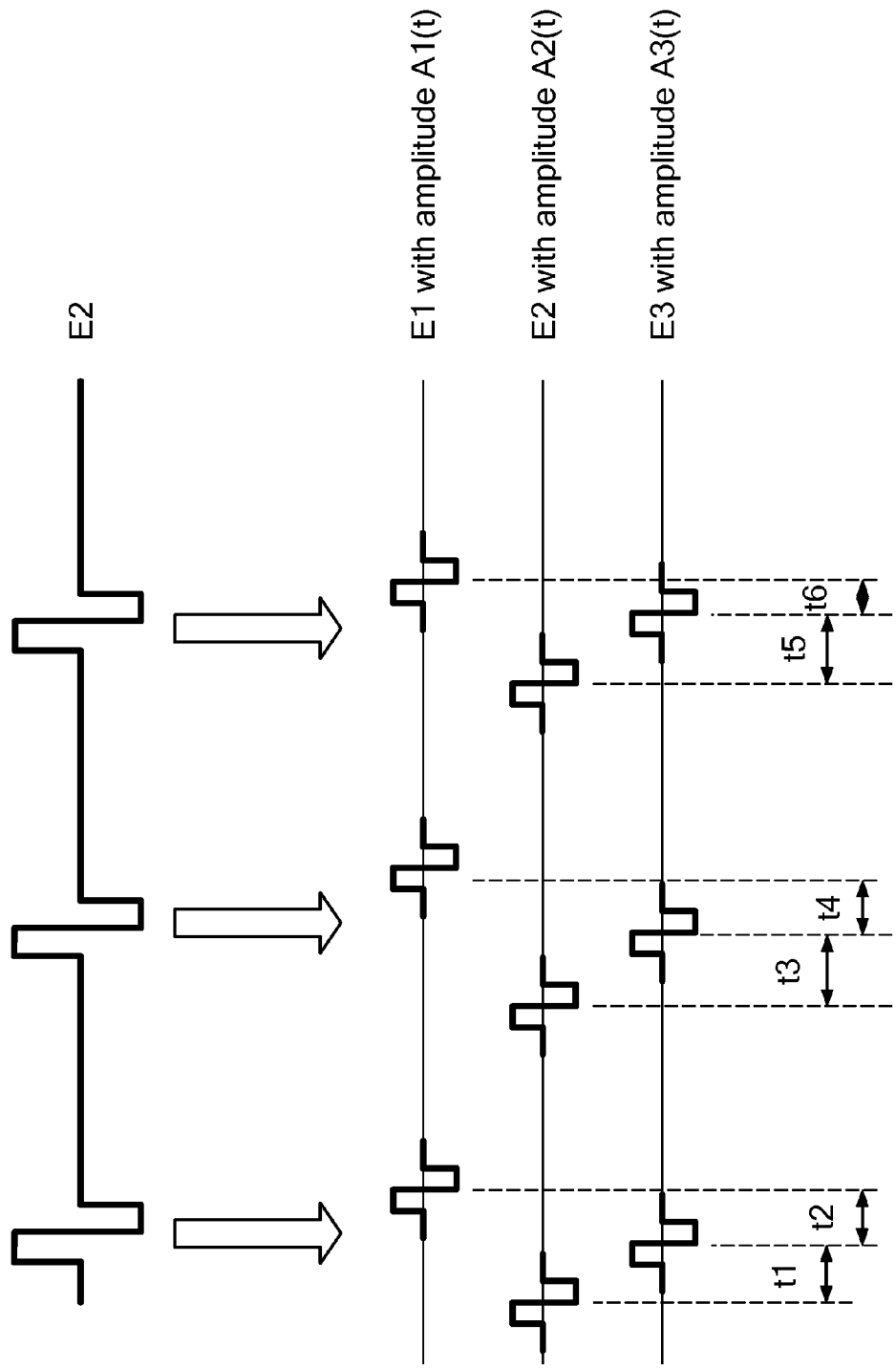
FIG. 3 illustratively shows a single pulse on an electrode channel that has been converted to a composite of three pulses on three electrode channels, in accordance with an embodiment of the invention.

FIG. 3 illustratively shows a single pulse on electrode channel E2 that has been converted to a composite of three pulses on channels E1, E2 and E3, in accordance with an embodiment of the invention. Temporal jitter between the pulses on channels E1, E2 and E3 has been introduced. The number of electrode channels upon which the composite of pulses is introduced is not limited to three; any number of channels may be utilized. The composite of pulses may utilize, to varying degrees, sequential and/or simultaneous stimulation.

The energy of each pulse composite may be substantially equal to the energy of the corresponding individual pulse out of the pulse sequence. Further, the center-of-mass of the composite pulses (spatial and/or temporal) may be presented where the individual pulse would have been presented in order to preserve the tonotopic order.

Parameters of the composite pulses that may be varied include, without limitation, amplitude distributions of the pulses within the pulse composites, the number of electrode channels used for the pulse composites, and pulse lengths of pulses within the pulse composites. Another parameter which may be varied is the temporal distributions between the pulses within the pulse composites. The jitter/time differentiation between the composite pulses may be of any duration. For example, the time differentiation may be, without limitation, on the order of μs or ms. The above-described distributions may be, without limitation, according to a Gaussian distribution, Poisson distribution and/or uniform distribution. All of the above-described parameters may also be varied between corresponding pulses of subsequent pulse composites.

In various embodiments of the invention, the jitter/time differentiation between the composite pulses may be based on one or more rules. Illustratively, there may be a predefined minimum time difference between the composite pulses. The minimum time difference between the composite pulses may be determined by the intensity of the original pulse (i.e., the corresponding individual pulse out of the pulse sequence). The minimum jitter/time differentiation may vary, so as to be, without limitation, dependent on the levels between the composite pulses to avoid masking effects. For example, if the original pulse is split into three pulses, the second of which has high intensity then the third may be masked if it is presented at a neighboring channel unless there is sufficient time between these two pulses.

In accordance with even more sophisticated embodiments of the invention, the representation of a single pulse out of the composite of pulses (provided this single pulse is suprathreshold) may further be represented by a sub-composite of pulses which includes sub- and/or supra-threshold pulses, preferable sub-threshold pulses only. All the variations of stimulation parameters explained above may be applied to this sub-composite as well.

The rate of the n individual pulses of the pulse sequence which is transformed into a composite of pulses may be the basis for a frequency/rate analysis that may be used to evaluate the quality of temporal coding for enhanced pitch discrimination. In various embodiments, the jitter of the composite pulses is solely used for better representation of this rate.

Figure 4:
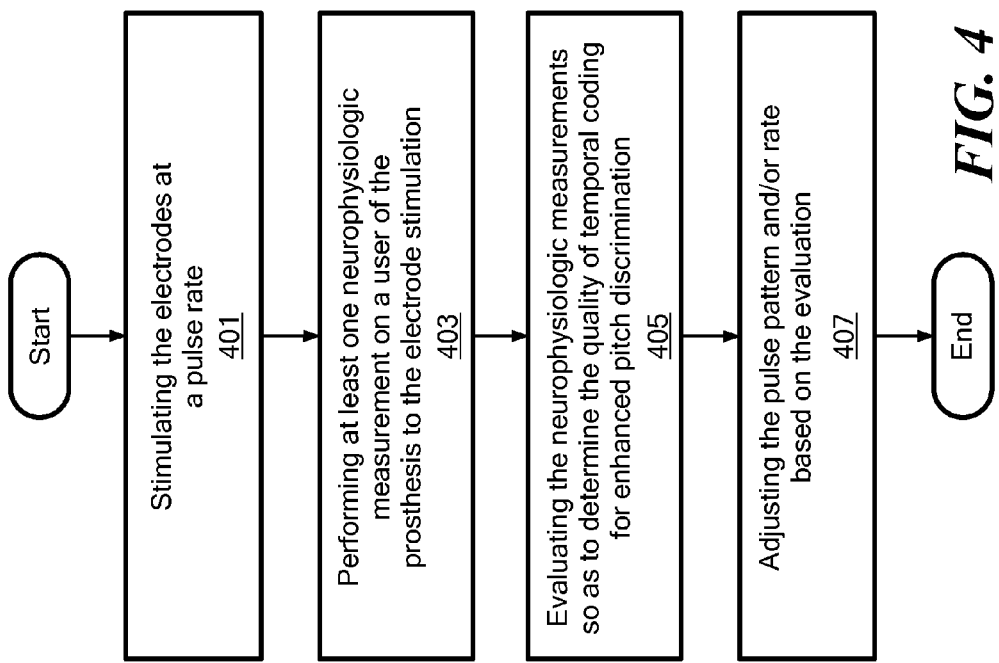
FIG. 4 shows a flow chart illustrating a method of evaluating the quality of temporal coding for enhanced pitch discrimination associated with an auditory prosthesis, in accordance with an embodiment of the invention.

FIG. 4 shows a flow chart illustrating a method of evaluating the quality of temporal coding for enhanced pitch discrimination associated with an auditory prosthesis, in accordance with an embodiment of the invention. The auditory prosthesis may include a plurality of electrodes in a multi-channel electrode array, and utilize, without limitation, the above-described pulse composite stimulation strategy; however other stimulation strategies (including, for example, CIS and/or simultaneous stimulation strategies) are within the scope of the present invention.

The electrodes of the prosthesis are stimulated at a pulse rate, step 401. At least one neurophysiologic measurement is then performed on a user of the prosthesis to the electrode stimulation, step 403. In various embodiments, the neurophysiological measurement may not require any subjective user feedback.

The neurophysiological test may include electrically evoked auditory steady state responses (EASSR) (see also: "Recording and online analysis of auditory steady state responses (ASSR) in Matlab", Andreas Bahmer, Uwe Baumann; Journal of Neuroscience Methods 187 (2010), 105-113, which is hereby incorporated herein by reference in its entirety; and "Temporal information transfer with cochlear implants: Improvements and Measurements", Habilitationsschrift, Andreas Bahmer, Frankfurt am Main, 2012, which is hereby incorporated herein by reference in its entirety). EASSR responses to low-rate pulse trains can be readily recorded by electrodes placed on the scalp of a cochlear implant user and separated from the artifacts generated by the electrical stimulation.

In further embodiments, the neurophysiological test may include electrically evoked brainstem response audiometry (EBERA) or near field measurement methods like electrically evoked compound action potentials (ECAP). The various measurement methodologies may allow following the effect of the composite pulses on temporal information transfer at a different levels of signal processing.

Referring back to FIG. 4, the neurophysiologic measurements are evaluated so as to determine the quality of temporal coding for enhanced pitch discrimination, step 405. The pulse pattern and/or rate may then be adjusted based on the evaluation, step 407, so as to provide optimal pitch discrimination for the user. Steps 405 and 407 may be repeated until a certain optimum is achieved (for example, convergence of a genetic algorithm).

The results of the neurophysiologic measurement may be evaluated by statistical tests. Illustratively, and without limitation, the results of the neurophysiologic measurement (particularly EASSR) may be evaluated using the following two statistical test paradigms. Both allow signal detection for a given significance threshold. A first test analyzes and compares Fourier components of several subsequent measurements at the frequency of the signal modulation (see, for example, "A new statistic for steady-state evoked potentials", Victor and Mast, Electroencephalography and Clinical Neurophysiology, 1991, 78:378-388, 1991, which is hereby incorporated herein by reference in its entirety). The second test evaluates Fourier components that are adjacent to the modulation frequency; these adjacent components are used to estimate the noise level (see, for example: "Human auditory steady-state responses to amplitude-modulated tones: phase and latency measurements" John and Picton, Hearing Research 141:57-79, 2000; and "MASTER: a Windows program for recording multiple", John and Picton, Computer Methods and Programs in Biomedicine 61 125-150, 2000, each of which is hereby incorporated herein by reference in its entirety). In addition, averaged data may be analyzed. Both test methods apply the F-test to estimate the probability that two subsets originate from the same probability distribution.

In further embodiments, the result of the neurophysiologic measurement (particularly EABR) may be evaluated by the conformation of Jewett peaks (height and width). The result of the neurophysiologic measurement (particularly ECAP) may be evaluated by the conformation of P1-N1 peaks (height and width).

A genetic algorithm may use the evaluation results for rating the quality of temporal information transfer (so-called "cost-function") for generation of a new set of parameters based on the previous sets of parameter (see, for example, "Parameters for a model of an oscillating neuronal network in the cochlear nucleus defined by genetic algorithms", Andreas Bahmer, Gerald Langner; Bio. Cybernetics (2010), 102:81-93, which is hereby incorporated herein by reference in its entirety).

Figure 1:
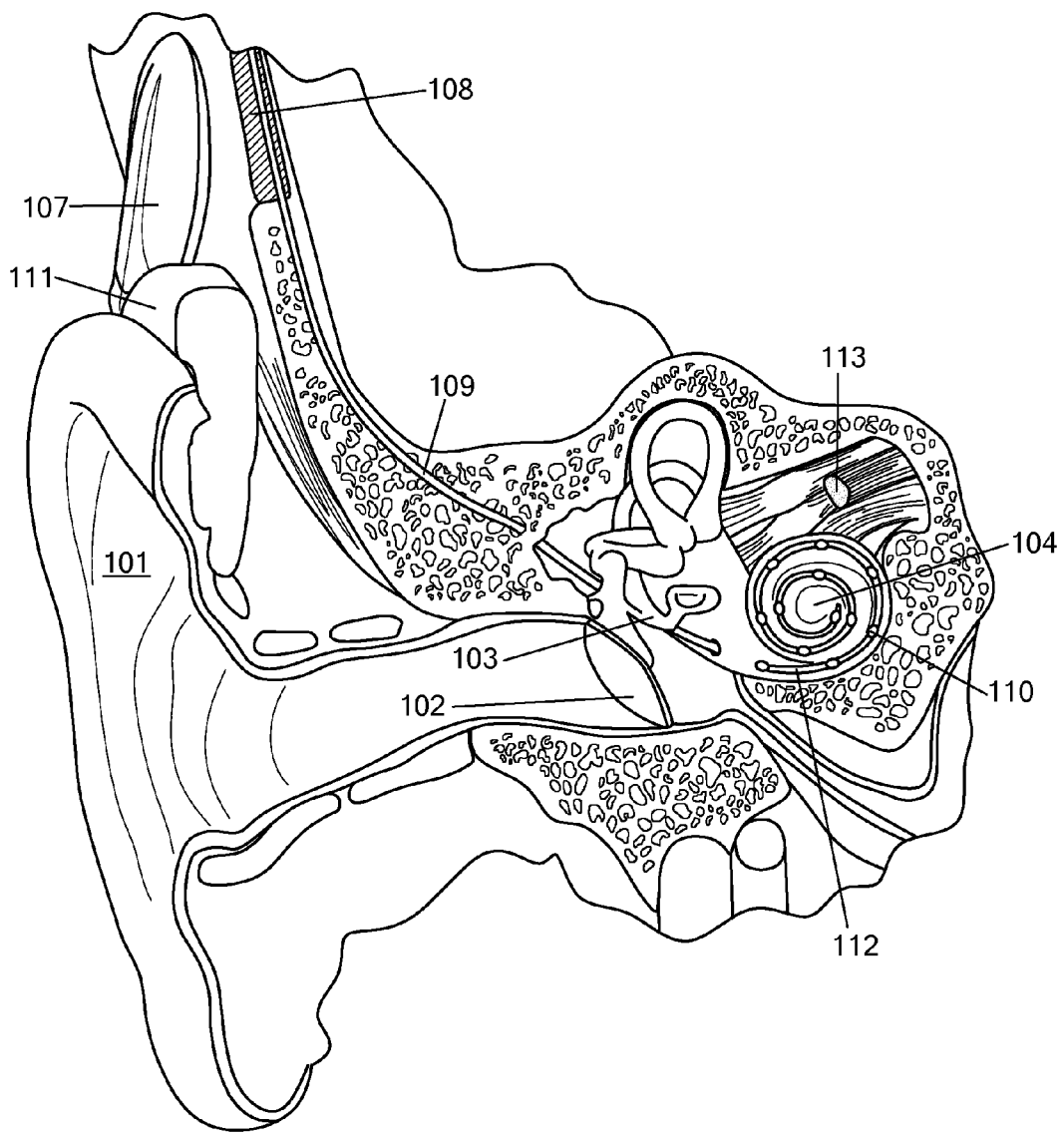
FIG. 1 shows anatomical structures and system components in a human ear having a cochlear implant system.
Figure 5:
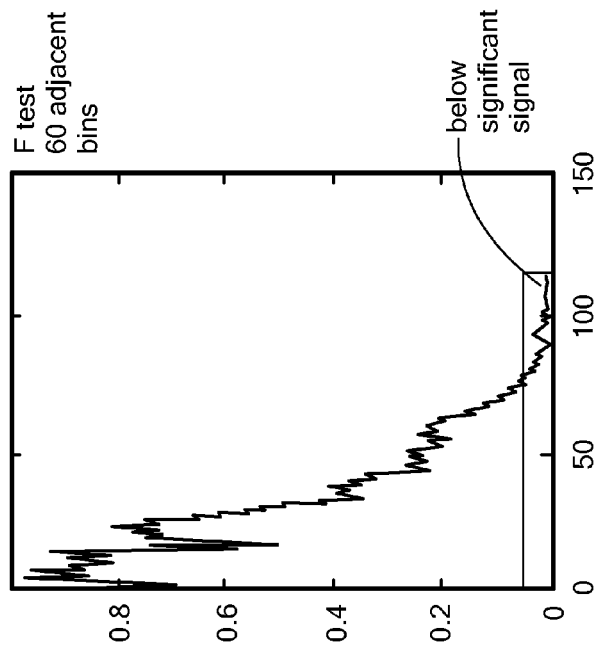
FIG. 5 shows an EASSR evaluated by statistical testing, in accordance with an embodiment of the invention.

Illustratively, FIG. 5 shows an EASSR evaluated by statistical testing, in accordance with an embodiment of the invention (see, for example, FIG. 1 F-test example for ASSR from Bahmer and Baumann, 2010). More particularly, FIG. 5 shows F Test probability when measuring ASSR with a normal hearing subject (x-axis: time [s], y-axis: test probability; headphone representation: sinusoidal amplitude modulated sine wave, carrier 1 kHz, modulation 97.656 Hz, 90 dB SPL). The F-test reaches significance after approximately 75 s (the straight line indicates alpha=0.05).

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of activating electrodes in a multi-channel electrode array, in which the electrodes of the multi-channel electrode array are spatially divided, the method comprising:
   determining a pulse for stimulating a single electrode of the electrode array;
   converting the pulse into a plurality of pulses for stimulating a plurality of electrodes in the electrode array, wherein the temporal and/or spatial center of mass for the plurality of pulses is substantially equivalent to that of the determined pulse; and
   stimulating the plurality of electrodes based, at least in part, on the converted pulses.

2. The method according to claim 1, wherein converting includes adding temporal separation between at least two pulses associated with different electrodes.

3. The method according to claim 2, wherein the pulses for stimulating a plurality of electrodes is at least one of a supra-threshold pulse and a sub-threshold pulse.

4. The method according to claim 1, wherein the energy of the plurality of pulses is substantially equal to the energy of the determined pulse for stimulating the single electrode.

5. The method according to claim 1, wherein the plurality of pulses vary in amplitude, pulse length, and/or temporal separation.

6. The method according to claim 1, wherein the pulse for stimulating a single electrode of the electrode array is one of a plurality of pulses that form a sequential pulse sequence for stimulating one or more electrodes in the electrode array.

7. The method according to claim 6, wherein the sequential pulse sequence is based on a Continuous Interleaved Sampling (CIS) speech signal processing strategy.

8. The method according to claim 6, further comprising, for at least one or more electrodes in the multi-channel electrode array different from the single electrode, repeating the steps of determining, converting and stimulating.

9. The method according to claim 8, wherein the electrode array is part of an auditory prosthesis that is implanted in a user, further comprising:
   performing at least one neurophysiologic measurement upon stimulating the electrodes;
   evaluating the neurophysiologic measurements so as to determine the quality of temporal coding for enhanced pitch discrimination.

10. The method according to claim 9, wherein the at least one neurophysiologic measurement includes electrically evoked auditory steady state responses (EASSR), electrically evoked brainstem response audiometry (EBERA), near field measurements, and/or electrically evoked compound action potentials (ECAP).

11. The method according to claim 1, wherein the multi-channel electrode is associated with an implant.

12. A method of activating electrodes in a multi-channel electrode array, in which the electrodes of the multi-channel electrode array are spatially divided, the method comprising:
   determining a pulse for stimulating a single electrode of the electrode array;
   converting the pulse into a plurality of pulses for stimulating a plurality of electrodes in the electrode array, wherein the plurality of pulses vary in amplitude, pulse length, and/or temporal separation, and wherein the variation is based on a Gaussian distribution, a Poisson distribution, and/or a uniform Distribution; and
   stimulating the plurality of electrodes based, at least in part, on the converted pulses.

13. The method according to claim 12, wherein converting includes adding temporal separation between at least two pulses associated with different electrodes.

14. The method according to claim 13, wherein the pulses for stimulating a plurality of electrodes is at least one of a supra-threshold pulse and a sub-threshold pulse.

15. The method according to claim 12, wherein the energy of the plurality of pulses is substantially equal to the energy of the determined pulse for stimulating the single electrode.

16. The method according to claim 12, wherein the pulse for stimulating a single electrode of the electrode array is one of a plurality of pulses that form a sequential pulse sequence for stimulating one or more electrodes in the electrode array.

17. The method according to claim 16, wherein the sequential pulse sequence is based on a Continuous Interleaved Sampling (CIS) speech signal processing strategy.

18. The method according to claim 12, further comprising, for at least one or more electrodes in the multi-channel electrode array different from the single electrode, repeating the steps of determining, converting, and stimulating.

19. The method according to claim 18, wherein the electrode array is part of an auditory prosthesis that is implanted in a user, further comprising:
   performing at least one neurophysiologic measurement upon stimulating the electrodes;
   evaluating the neurophysiologic measurements so as to determine the quality of temporal coding for enhanced pitch discrimination.

20. The method according to claim 19, wherein the at least one neurophysiologic measurement includes electrically evoked auditory steady state responses (EASSR), electrically evoked brainstem response audiometry (EBERA), near field measurements, and/or electrically evoked compound action potentials (ECAP).

21. The method according to claim 12, wherein the multi-channel electrode is associated with an implant.

22. A method of activating electrodes in a multi-channel electrode array that is part of an auditory prosthesis that is implanted in a user, in which the electrodes of the multi-channel electrode array are spatially divided, the method comprising:
   determining a pulse for stimulating a single electrode of the electrode array wherein the pulse for stimulating a single electrode of the electrode array is one of a plurality of pulses that form a sequential pulse sequence for stimulating one or more electrodes in the electrode array;
   converting the pulse into a plurality of pulses for stimulating a plurality of electrodes in the electrode array;
   stimulating electrodes in the multi-channel electrode array based, at least in part, on the converted pulses and the sequential pulse sequence;
   performing at least one neurophysiologic measurement upon stimulating the electrodes; and
   evaluating the neurophysiologic measurements so as to determine the quality of temporal coding for enhanced pitch discrimination, wherein evaluating the neurophysiologic measurements includes statistical testing.

23. The method according to claim 22, wherein evaluating the neurophysiologic measurements includes using a genetic algorithm.

24. The method according to claim 22, wherein converting includes adding temporal separation between at least two pulses associated with different electrodes.

25. The method according to claim 24, wherein the pulses for stimulating a plurality of electrodes is at least one of a supra-threshold pulse and a sub-threshold pulse.

26. The method according to claim 22, wherein the energy of the plurality of pulses is substantially equal to the energy of the determined pulse for stimulating the single electrode.

27. The method according to claim 22, wherein the plurality of pulses vary in amplitude, pulse length, and/or temporal separation.

28. The method according to claim 27, wherein the variation is based on a Gaussian distribution, a Poisson distribution, and/or a uniform Distribution.

29. The method according to claim 22, wherein the sequential pulse sequence is based on a Continuous Interleaved Sampling (CIS) speech signal processing strategy.

30. The method according to claim 22, wherein the at least one neurophysiologic measurement includes electrically evoked auditory steady state responses (EASSR), electrically evoked brainstem response audiometry (EBERA), near field measurements, and/or electrically evoked compound action potentials (ECAP).

31. The method according to claim 22, wherein the sequential pulse sequence has a pulse rate, the method further comprising adjusting the pulse rate based on the evaluation.

32. The method according to claim 22, further comprising, for at least one or more electrodes in the multi-channel electrode array different from the single electrode, repeating the steps of determining and converting, and wherein stimulating further includes stimulation based, at least in part, on converted pulses associated with the at least one or more electrodes in the multi-channel electrode array different from the single electrode.

33. A method of activating electrodes in a multi-channel electrode array that is part of an auditory prosthesis that is implanted in a user, in which the electrodes of the multi-channel electrode array are spatially divided and in which the electrodes are stimulated at a pulse rate, the method comprising:
determining a pulse for stimulating a single electrode of the electrode array wherein the pulse for stimulating a single electrode of the electrode array is one of a plurality of pulses that form a sequential pulse sequence for stimulating one or more electrodes in the electrode array, the sequential pulse sequence having a pulse rate;
converting the pulse into a plurality of pulses for stimulating a plurality of electrodes in the electrode array;
stimulating electrodes in the multi-channel electrode array based, at least in part, on the converted pulses and the sequential pulse sequence;
performing at least one neurophysiologic measurement upon stimulating the electrodes;
evaluating the neurophysiologic measurements so as to determine the quality of temporal coding for enhanced pitch discrimination; and
adjusting the pulse rate based on the evaluation.

34. The method according to claim 33 wherein converting includes adding temporal separation between at least two pulses associated with different electrodes.

35. The method according to claim 34, wherein the pulses for stimulating a plurality of electrodes is at least one of a supra-threshold pulse and a sub-threshold pulse.

36. The method according to claim 33, wherein the energy of the plurality of pulses is substantially equal to the energy of the determined pulse for stimulating the single electrode.

37. The method according to claim 33, wherein the plurality of pulses vary in amplitude, pulse length, and/or temporal separation.

38. The method according to claim 37, wherein the variation is based on a Gaussian distribution, a Poisson distribution, and/or a uniform Distribution.

39. The method according to claim 33, further comprising, for at least one or more electrodes in the multi-channel electrode array different from the single electrode, repeating the steps of determining and converting, and wherein stimulating further includes stimulation based, at least in part, on converted pulses associated with the at least one or more electrodes in the multi-channel electrode array different from the single electrode.

40. The method according to claim 33, wherein the sequential pulse sequence is based on a Continuous Interleaved Sampling (CIS) speech signal processing strategy.

41. The method according to claim 33, wherein the at least one neurophysiologic measurement includes electrically evoked auditory steady state responses (EASSR), electrically evoked brainstem response audiometry (EBERA), near field measurements, and/or electrically evoked compound action potentials (ECAP).

42. The method according to claim 33, wherein evaluating the neurophysiologic measurements includes using a genetic algorithm.

43. An auditory prosthesis system comprising:
a stimulator adapted to be implantable, the stimulator including a plurality of electrodes forming a multi-channel electrode array; and
a processor configured to:
determine at least one pulse for stimulating a single electrode of the electrode array; and
convert each of the pulses into a plurality of pulses for stimulating a plurality of electrodes in the electrode array; and
a test module configured to perform at least one neurophysiologic measurement on a user of the prosthesis to the electrode stimulation, the test module further configured to evaluate the neurophysiologic measurements so as to determine the quality of temporal coding for enhanced pitch discrimination.

44. The system according to claim 43, wherein the processor is configured to add temporal separation between at least two converted pulses associated with different electrodes.

45. A method of evaluating the quality of temporal coding for enhanced pitch discrimination associated with a auditory prosthesis, the auditory prosthesis including a plurality of electrodes in a multi-channel electrode array, the method including:
stimulating the electrodes at a pulse rate;
performing at least one neurophysiologic measurement on a user of the prosthesis to the electrode stimulation;
evaluating the neurophysiologic measurements so as to determine the quality of temporal coding for enhanced pitch discrimination; and
adjusting the pulse pattern and/or rate based on the evaluation.

46. The method according to claim 45, wherein performing the at least one neurophysiologic measurement is done without subjective feedback from the user.

47. The method according to claim 45, wherein the at least one neurophysiologic measurement includes electrically evoked auditory steady state responses (EASSR), electrically evoked brainstem response audiometry (EBERA), near field measurements, and/or electrically evoked compound action potentials (ECAP).

48. The method according to claim 45, wherein evaluating the neurophysiologic measurements includes statistical testing or a genetic algorithm, or both.

49. An auditory prosthesis system comprising:
a plurality of electrodes in a multi-channel electrode array:
a stimulator for stimulating the electrodes at a pulse rate;
means for performing at least one neurophysiologic measurement on a user of the prosthesis to the electrode stimulation;
means for evaluating the neurophysiologic measurements so as to determine the quality of temporal coding for enhanced pitch discrimination; and
means for adjusting the pulse pattern and/or rate based on the evaluation.

50. The system according to claim 49, wherein the means for performing the at least one neurophysiologic measurement is done without subjective feedback from the user.

* * * * *